United States Patent
Deumal Rubio et al.

(10) Patent No.: US 9,907,311 B2
(45) Date of Patent: Mar. 6, 2018

(54) ANTI-ODOUR AND ANTIBACTERIAL FABRIC IN TEXTILE GOODS

(71) Applicant: SUTRAN I MAS D, S.L., Badalona (Barcelona) (ES)

(72) Inventors: Oscar Deumal Rubio, Canet de Mar (ES); David Cahisa Gallardo, L'Hospitalet de Llobregat (ES); Alejandro Robas Cobos, Badalona (ES); Xiaozhang Wang, Badalona (ES)

(73) Assignee: SUTRAN I MAS D, S.L., Badalona (Barcelona) (ES)

( * ) Notice: Subject to any disclaimer, the term of this patent is extended or adjusted under 35 U.S.C. 154(b) by 0 days.

(21) Appl. No.: 14/298,727

(22) Filed: Jun. 6, 2014

(65) Prior Publication Data
US 2015/0064280 A1 Mar. 5, 2015

(30) Foreign Application Priority Data
Jun. 7, 2013 (ES) .................................. 201330854

(51) Int. Cl.
| | | |
|---|---|---|
| *A01N 59/16* | (2006.01) | |
| *A01N 59/06* | (2006.01) | |
| *A41B 11/00* | (2006.01) | |
| *A41B 9/00* | (2006.01) | |
| *A41B 9/04* | (2006.01) | |
| *D06M 11/44* | (2006.01) | |
| *D06M 11/45* | (2006.01) | |
| *D06M 11/50* | (2006.01) | |
| *D06M 11/83* | (2006.01) | |
| *D06M 13/00* | (2006.01) | |
| *D06M 16/00* | (2006.01) | |

(52) U.S. Cl.
CPC ............. *A01N 59/16* (2013.01); *A01N 59/06* (2013.01); *A41B 9/001* (2013.01); *A41B 9/04* (2013.01); *A41B 11/00* (2013.01); *A41B 11/005* (2013.01); *D06M 11/44* (2013.01); *D06M 11/45* (2013.01); *D06M 11/50* (2013.01); *D06M 11/83* (2013.01); *D06M 13/005* (2013.01); *D06M 16/00* (2013.01)

(58) Field of Classification Search
None
See application file for complete search history.

(56) References Cited

U.S. PATENT DOCUMENTS

| | | | | |
|---|---|---|---|---|
| 5,928,720 A | * | 7/1999 | Kuhn | .................... D06M 11/45 427/190 |
| 2010/0047303 A1 | * | 2/2010 | Yhlen | .................... A61L 15/18 424/409 |
| 2010/0113537 A1 | * | 5/2010 | Nonaka | ......................... 514/358 |
| 2011/0054430 A1 | * | 3/2011 | Wastlund-Karlsson | ............. A61F 13/8405 604/375 |

* cited by examiner

*Primary Examiner* — Carlos A Azpuru
*Assistant Examiner* — Casey S Hagopian
(74) *Attorney, Agent, or Firm* — Dowell & Dowell, PC

(57) ABSTRACT

This Invention Patent application consists of a fabric to be used in textile applications, which makes those items more comfortable and increases their bactericidal capacity, both in the number of types that it fights, and in the time that this capacity is effective, using a mixture of fibers and performing a series of treatments prior to the final manufacture of the textile goods that reinforce the properties of the fabric.

2 Claims, No Drawings

ANTI-ODOUR AND ANTIBACTERIAL FABRIC IN TEXTILE GOODS

OBJECT OF THE INVENTION

This Invention Patent application consists of a fabric to be used in textile applications, having properties to combat odours and bacteria proliferation.

STATE OF THE ART

Various types of materials are currently used to avoid the creation of odours, as well as the proliferation of bacteria, which also cause odours.

In order to obtain these materials, the fibres that make up the fabric are bathed in metallic elements such as silver and/or copper so that particles of said elements adhere to the fibres, with the allergic reactions that these substances can cause to some people if they are used in contact with human or animal skin. There are also baths that coat the fibres with zinc ions, which possess the property of not reacting aggressively with the clothing wearer's skin.

On the other hand, this type of fabric, with these baths, quickly lose the antibacterial elements, which makes them susceptible once again to the presence of bacteria and odours, as the fibres do not retain the silver and/or copper ions.

Thus there are known fabrics that are treated, once they are made into textiles, with baths in products that allow antibacterial elements to adhere to their fibres and eliminate odours, which quickly lose their effectiveness. And as a fabric, they have the usual properties of fabrics made of cotton and other known fibres, especially regarding their ability to absorb water, the feel and the stiffness of the fabric.

DESCRIPTION OF THE INVENTION

The purpose of the invention is to obtain a fabric to be used in textile goods commonly used by people, making those items more comfortable and increasing their antibacterial quality, both in the number of types that it fights, and in the time that this quality is effective.

And so the invention takes the form of a fabric for use in textile goods, preferably for people, made up of a mixture of synthetic and natural fibres, and of an antibacterial fibre made up of cellulose and a zinc-based compound. This mixture that makes up the thread has a percentage of antibacterial fibre of 8% to 70%.

The antibacterial cellulose fibre has the element zinc on the inside of it, so that it has the properties of said zinc against odours and the proliferation of bacteria. Its effects last over time in spite of washing, as it is located on the inside of the fibre and not adhered to it, the latter case allowing it to come off very easily with washing, causing a loss of its features.

As well as this substratum, whether it is fibre, thread, or fabric, it is also given a bath of an aluminium derivative that has an effect on the fabric's ability to absorb water, increasing the speed with which the fabric absorbs water. This goes along with an ability to absorb water, or sweat (in the practical use of the fabric) that the antibacterial fibre has, producing a fabric with a greater ability to absorb water than existing fabrics.

This ability to absorb water is a measure of the comfort of the fabric, as greater absorption of water gives a greater feeling of comfort, as the wearer's sweat is eliminated.

The aluminium bath also gives the fabric a greater feeling of softness, increasing the user of said fabric's perception of comfort.

On the other hand, antibacterial fibre added to cotton, wool or similar fibres makes the composition of the thread such that fabrics made up of these fibres are less stiff than those made purely of cotton, wool or similar fibres. This lesser stiffness increases the comfort of the fabric, as the less stiff the fabric is, the more comfortable it is considered.

By means of a new treatment on the thread or fabric that is the subject of the present patent, said fabric undergoes the addition of a derivative of hydrogen peroxide that allows it to be added to the structure of the fabric itself, making it more antibacterial, as well as antifungal, as well as antiviral, and with the property of avoiding the formation of algae and spores.

With this treatment, added to the properties of the zinc, and with the particularity that said zinc is located on the inside of the fibre, we have a fabric with an antibacterial fibre that is reinforced by the action of said compound, obtaining a fabric that is much safer for the user's health than fabrics with metallic ions adhered to the fibres.

The fabric is produced with less water consumption, as the antibacterial fibre used consumes twenty times less water than the production of cotton thread, lowering the environmental load to 0.6.

The application of the fabric is aimed at the making of items that preferably correspond to socks, although hose, underwear, and fabrics for medical-healthcare items and household linens will also be made.

In this manner, a fabric is obtained that clearly improves the features offered until now by existing fabrics for the purpose of eliminating odours, as it is more comfortable, thanks to greater water absorption, a nicer feel, and less stiffness in the thread, also achieving an antibacterial action that lasts much longer, all with less strain on the environment.

Other details and features will be set out over the course of the description below, showing a practical manufacture of the invention as an illustration, without limiting it to that use.

DESCRIPTION OF AN EMBODIMENT OF THE INVENTION

In one of the preferred forms of the invention, we have obtained a fabric for use in textile goods, applied preferably to socks, hose, underwear, other health applications, household linens, etc., to avoid odours, possible bacteria, and to increase the comfort of the same.

This fabric is made up of a mixture of fibres, where usually this mixture that makes up the thread has cotton fibre and an antibacterial fibre with a percentage of the latter of between 8% and 70%.

This antibacterial fibre is made up of cellulose and derivatives of zinc oxide, wherein said zinc is incorporated into the structure of the fibre itself, usually through extrusion, to be given off in a way that it lasts through washing, withstanding up to around 75 washings, so it may be said that the useful properties of said fibre last practically throughout the life of a sock.

This mixture of fibres for creating the fabric provides a thread stiffness of 69 cN/%, whereas a 22/1 Ne made of cotton has a stiffness of 78 cN/%.

The cellulose composition of the antibacterial fibre that forms a part of the mixture of fibres of the fabric increases the property of water absorption, so that for a cotton fabric a test of water absorption at 37° C. and 75% humidity scores 7.7%, whereas for the fabric indicated, with minimum values of 20% of antibacterial fibre, the score is 11%.

The fabric treated with an aluminium derivative allows the fabric to absorb water more quickly than a cotton fabric, reducing the time of absorption by at least 30%.

The stiffness of the fabric, its ability to absorb water, and the speed at which it does so allow for a very comfortable fabric, superior to cotton fabrics, for instance, as has already been shown; the greater the absorption, the greater the feeling of comfort.

Besides its composition and the previous aluminium treatment, the fabric also undergoes a treatment wherein a hydrogen peroxide derivative is added to its structure, which is given off as the fabric is used, allowing a great antibacterial, antifungal, and antiviral action, also avoiding the formation of algae and spores. The types of bacteria that its development avoids widens those avoided by the zinc of the fibre itself, and among others, they are:

Gram-positive bacteria: *Staphilococcus Aureus, Corynebacterium Diptheriae, Listeria Monocytogenes, Streptococci, Micrococcus Luteus*, MRSA and *Enterococcus Faecium*.

Gram-negative bacteria: *Eschericha Coli, Klebsiella Pneumoniae, Pseudomonas Aeruginosa, Salmonella Choleraesuis, Proteus Vulgaris, Serratia Marcescens, Proteus Mirabilis*.

With this treatment, families of fungi are also eliminated, such as:

*Aspergillus Niger, Cladosporium* spp, *Trichophyton mentagrophites, Candida Albicans, Penicillium Citrinum, Fusarium Solani, Alternaria* spp.

Besides this, it also avoids the formation of some types of algae and spores, as well as its action against some viruses, such as Influenza A (H1N1), Rhinovirus, Herpes Simplex and Feline Calicivirus.

Preferably, fabric is used for making socks, although hose, underwear, and fabrics for medical-healthcare items and household linens will also be made. In the making of socks, cellulose antibacterial fibres of a length of 20 mm to 100 mm are used, and of a thickness of 1 dtex to 8 dtex.

Having sufficiently described this invention, it is easy to see that any sort of modification deemed necessary can be introduced as long as they do not change the essence of the invention, which is summarised in the following claims:

The invention claimed is:

1. An anti-odor and antibacterial fabric for textile goods made up of a mixture of fibres and giving off zinc to perform the function of avoiding odors and eliminating bacteria, wherein the mixture of fibres having at least one type of antibacterial fibre made up of cellulose and a derivative of zinc oxide, with the zinc oxide derivative on the inside of a structure of the at least one type of antibacterial fibre wherein the proportion of the mixture of fibres of the fabric is made up of a percentage of antibacterial fibre between 8% and 70%, the rest of the fibers being natural and synthetic fibres, and the fabric structure being treated with a hydrogen peroxide derivative and an aluminum derivative, incorporated by subjecting the fabric to a bath, so that the mixture of fibres provides a thread stiffness of 69 CN %, and so that the fabric absorbs water more quickly than a cotton fabric.

2. The anti-odor and antibacterial fabric for textile goods according to the claim 1, wherein the fabric is used for making socks, hose, underwear, medical-healthcare items and household linens.

* * * * *